United States Patent [19]

Akasaka et al.

[11] Patent Number: 4,801,539

[45] Date of Patent: Jan. 31, 1989

[54] FERMENTATION METHOD FOR PRODUCING HYALURONIC ACID

[75] Inventors: Hidemichi Akasaka; Hisayuki Komasaki; Takayuki Arai, all of Yokohama, Japan

[73] Assignee: Shiseido Company Ltd., Japan

[21] Appl. No.: 732,267

[22] Filed: May 9, 1985

[30] Foreign Application Priority Data

May 25, 1984 [JP] Japan .................................. 59-105942

[51] Int. Cl.$^4$ .......................... C12P 19/04; C12R 1/46; C07H 5/06; C08B 37/00
[52] U.S. Cl. .................................... 435/101; 435/885; 536/55.1; 536/55.3
[58] Field of Search ....................... 435/101, 885, 253; 536/55.1, 55.2, 123, 55.3

[56] References Cited

U.S. PATENT DOCUMENTS 4,517,295  5/1985  Bracke et al. ...................... 536/55.1

FOREIGN PATENT DOCUMENTS 0037001  3/1983  Japan .................................. 536/55.1

OTHER PUBLICATIONS

Buchanan et al., "Recovery of Microorganisms from Synovial and Pleural Fluids of Animals using Hyperosmolar Media", *Veterinary Microbiology*, v. 7 (1982); pp. 19–33.
B. Holmström, Appl. Microbial, 15 (6), 1409–1413 (1967).
J. B. Woolcock, J. Gem. Microbial, 85, 372–375 (1974).
E. Kjem, Acta Pathol. Microbial. Scand., 84(3), 162–164 (1976).

*Primary Examiner*—Elizabeth C. Weimar
*Attorney, Agent, or Firm*—Wegner & Bretschneider

[57] ABSTRACT

Streptolysin-free hyaluronic acid is produced by cultivating a microorganism belonging to a genus Steptococcus which is anhemolytic and is capable of producing hyaluronic acid (e.g., *Streptococcus zooepidemicus* FERM BP-784) in a culture medium.

5 Claims, 2 Drawing Sheets

FERMENTATION METHOD FOR PRODUCING HYALURONIC ACID

BACKGROUND OF THE INVENTION

1. Field of the Invention

The present invention relates to a fermentation method for producing hyaluronic acid. More specifically, it relates to a fermentation method for producing streptolysin-free hyaluronic acid by cultivating (or incubating) a microorganism belonging to genus Streptococcus.

2. Description of the Related Art

Hitherto, Hyaluronic acid has been isolated from the hyaloid liquid of bovine eyes, cockscombs, umbilici, and articulation liquid of chickens and is known to be used as a substance which maintains a jelly state by bonding with proteins or the other mucopolysaccharides and water to thereby act as a lubricant, to prevent the invasion of bacteria, and retain water. However, the above method is disadvantageous in that the cost of obtaining the hyaluronic acid is too high.

It has been reported in, for example, B. Holmström, Appl. Microbial, 15(6), 1409–1413, 1967, J. B. Woolcock, J. Gen. Microbial, 85, 372–375, 1974, and E. Kjem, Acta Pathol. Microbial. Scand, 84(3), 162–164, 1976 that hyaluronic acid can be produced relatively cheaply by utilizing bacteria strains belonging to the genus Streptococcus such as *Streptococcus pyogenes, Streptococcus equi, Streptococcus equisimilis, Streptococcus dysgalactiae,* and *Streptococcus zooepidemicus*. However, according to Bergey's Manual of Determinative Bacteriology (8th edition, 1974), all of the above-mentioned strains belong to biogenic groups of genus Streptococcus, such as lactic acid and A or C type bacteria of a Lancefield serum group. That is, these strains are bacteria generally known as hemolytic streptococci, and are known to exhibit $\beta$-hemolysis by soluble hemolysin, i.e., streptolysin. Although correlationship between the streptolysin producing capability and the pathogenicity is not clearly understood, the hyaluronic acid product is likely to be unpreferably contaminated with the above-mentioned proteins when hyaluronic acid is industrially produced from the cultivation of the above-mentioned strains. Especially, when wishing to incorporate hyaluronic acid into medical compositions for external use or into cosmetic compositions, it is preferable that streptolysin be completely removed from the hyaluronic acid product since these compositions are applied to the skin.

When subculturing of the above-mentioned strains is continued, not only is the hemolysis gradually decreased but also the hyaluronic acid producing capability is decreased, and the mucoid colonies disappear. Furthermore, the hemolysis of the strains still remains after repeated subculturing. Consequently, it is very difficult or almost impossible to effectively produce hyaluronic acid not contaminated by streptolysin.

SUMMARY OF THE INVENTION

Accordingly, the objects of the present invention are to eliminate the above-mentioned disadvantages and to provide a fermentation method for producing hyaluronic acid not containing streptolysin.

Another object of the present invention is to find a microorganism which is anhemolytic and is capable of effectively producing hyaluronic acid.

Other objects and advantages of the present invention will be apparent from the following description.

In accordance with the present invention, there is provided a fermentation method for producing streptolysin-free hyaluronic acid comprising the steps of (i) cultivating a mircroorganism belonging to a genus Streptococcus which is anhemolytic and is capable of producing hyaluronic acid in a culture medium and (ii) isolating streptolysin-free hyaluronic acid from the cultivated product.

BRIEF DESCRIPTION OF THE DRAWING

The present invention will be better understood from the description set forth below with reference to the accompanying drawings, in which.

DESCRIPTION OF THE PREFERRED EMBODIMENTS

Figure 1:
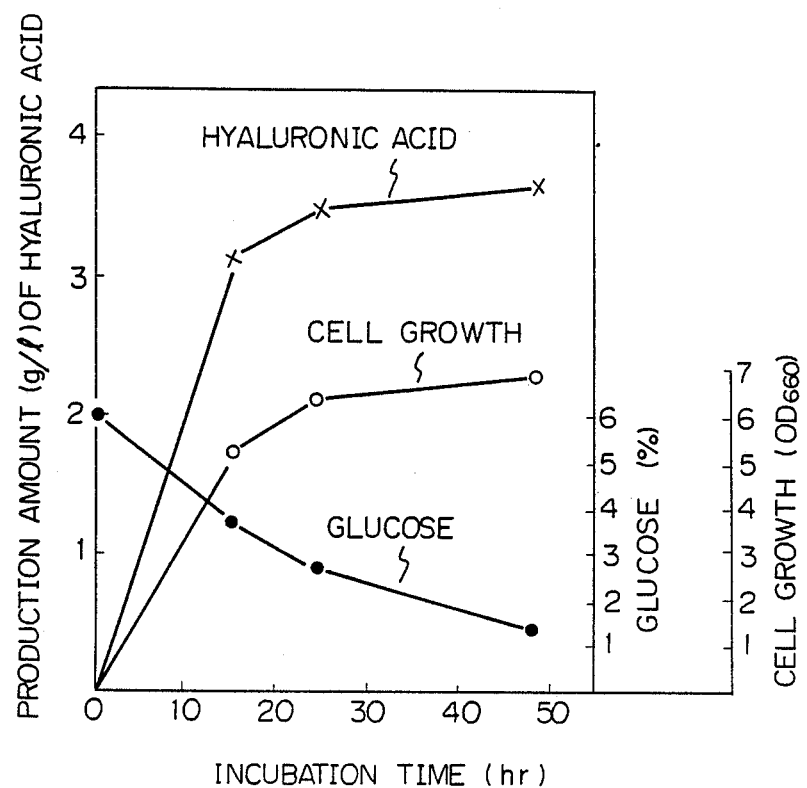
FIG. 1 graphically illustrates the correlationship between the production amount (g/l) of hyaluronic acid, the glucose amount (%), or the cell growth (OD660), and the cultivation time (hr) during the cultivation in Example 2.

The microorganisms usable in the fermentation according to the present invention are mutants belonging to genus Streptococcus which are anhemolitic and are capable of producing hyaluronic acid. A typical example of such a mutant is *Streptococcus zooepidemicus* NH-131 which is an anhemolytic mutant of a strain belonging to *Streptococcus zooepidemicus* and which has been deposited since April 14, 1984 in the Fermentation Research Institute (FRI) in Japan as FERM P-7580 and transferred to the Fermentation Research Institute (FRI) (i.e., International Depository Authority under Budapest Treaty at Tsukuba in Japan) as FERM BP-784 under the Budapest Treaty.

The strain *Streptococcus zooepidemicus* NH-131 has been isolated from the strain *streptococcus zooepidemicus* obtained from the tunica conjunctiva bulbi of a guinea pig as shown in Example 1.

The anhemolytic mutants of *Streptococcus zooepidemicus* can be selectively isolated as follows. That is, the cells of the strain *Streptococcus zooepidemicus* are subcultured to select the cells of the strain having decreased or reduced hemolysis. The selected cells are subjected to a conventional mutation treatment by using ultraviolet (UV) light or N-methyl-N'-nitro-N-nitrosoguanidine (i.e., NTG). The cells thus treated as spread on a blood agar medium and, after growth, mutants having anhemolysis and capable of forming viscous colonies are selectively collected. Thus, the desired mutants can be obtained.

The morphological characteristics of the *Streptococcus zooepidemicus* NH-131 are shown below. The *Streptococcus zooepidemicus* NH-131 mutant has substantially the same morphological characteristics as those of the parent strain *Streptococcus zooepidemicus* as set forth in Bergey's Manual of Determinative Bacteriology, 8th edition, p498 (1974), except that the strain NH-131 is gram positive and $\beta$-hemolytic($-$) streptococcus and forms transparent viscous colonies on a sheep blood agar medium.

(1) Gram stain: $+$
(2) $\beta$-Hemolysis: $-$
(3) Thermal resistance at 60° C. for 30 min.: $-$
(4) Resistance against 40% bile: $-$ (5) Resistance against 6.5% salt: —
(6) Alkali resistance at pH of 9.6: —
(7) Decomposability against sodium hippurate: —
(8) Decomposability against esculin: —
(9) Solubility in gelatin: —
(10) Sensibility on bacitracin: +
(11) Decomposability of sugar
   Glucose: +
   Maltose: ±
   Lactose: —
   Sucrose: +
   Sorbitol: —
   Salicin: —
   Glycerol: —
   Mannitol: —
   Trehalose: —

Remarks

+: positive
±: pseudopositive
—: negative

The *Streptococcus zooepidemicus* mutants according to the present invention can be cultivated or grown in a culture medium preferably containing carbon sources, inorganic salts, and optional organic trace nutrients. Examples of such carbon sources are organic acids and aliphatic alcohols. According to the present invention, carbon sources containing sugars such as starch hydrolysates, glucose, sucrose, galactose, and fructose can be preferably used. Typical examples of the nitrogen sources are ammonium sulfate, sodium nitrate, ammonium secondary phosphate (i.e., diammonium hydrogenphosphate), meat extract, peptone, mixtures of various amino acids, and yeast extract. In addition to these components, sodium chloride, magnesium, potassium, iron, calcium, and other metal salts of phosphoric acid, sulfuric acid, and carbonic acid, and vitamins can be optionally added if desired.

The sugars can be added all at once to a culture medium. However, the sugars can be more advantageously added to a culture medium in small portions, to thereby increase the yield of hyaluronic acid.

The cultivation according to the present invention can be carried out preferably under aerobic conditions by, for example, a shaking culture or an aeration spinner culture at a temperature of, for example, 30° C. to 37° C. When the cultivation is carried out by adjusting the pH of the medium to 5.5 to 9.0 with an aqueous alkaline solution, the desired hyaluronic acid can be stably produced in a large amount. Examples of the aqueous alkaline solutions are one or more conventional alkaline compounds such as sodium hydroxide, potassium hydroxide, basic amino acids, and lower amines.

After cultivation, the hyaluronic acid accumulated in the cultivated mixture can be recovered by conventional methods for the separation and purification of polysaccharides. However, acidification of the cultivated mixture prior to the recovery is preferable in that the purity of the hyaluronic acid thus recovered is increased.

For example, the hyaluronic acid can be isolated from the cultivated mixture as follows. The cells and the other insoluble components in the cultivated mixture are first removed by filtration or centrifugal separation. Then, the proteins contained in the resultant filtrate are removed by, for example, trichloroacetic acid or a mixture of chloroform and isoamyl alcohol, an adsorbent such as activated carbon or activated clay, or a protein decomposition enzyme such as pepsin, papain or pronase. The low molecular weight contaminants remaining in the cultivated mixture are removed by ultrafiltration, dialysis, organic solvent addition precipitation methods, a cationic surfactant, or an adsorption method using an ion exchange resin. The desired hyaluronic acid can be recovered from the resultant cultivated mixture by, for example, a freeze drying, spray drying or organic solvent precipitation method.

According to the present invention, the desired streptolysin-free hyaluronic acid can be produced at a high yield. Accordingly, the hyaluronic acid produced according to the present invention can be advantageously incorporated into medical compositions for external use and cosmetic compositions which are applied to the skin.

EXAMPLES

The present invention will now be further illustrated by, but is by no means limited to, the following Examples, wherein "percents" are all by weight unless otherwise specified.

Example 1

The cells of *Streptococcus zooepidemicus* isolated from the tunica conjunctiva bulbi of guinea pigs were cultivated at a temperature of 37° C. in a brain heart infusion medium (available from Eiken Kagaku Co., Japan). The cells during the logarithmic growth phase were collected and the centrifugal separation was repeated at a low temperature, and the separated cells were sterilized by washing twice with a 1/20 M phosphate buffer solution. The cells, thus obtained were shaken at a temperature of 37° C. for 20 minutes in 1/20 M phosphate buffer solutions containing 100 to 500 µg/ml and were then cooled on ice. The cells were washed twice with 1/20 M phosphate buffer at a low temperature and were then inoculated into a brain heart infusion medium. The cultivation was carried out at a temperature of 37° C. for 24 hours. Thus, a mutant was obtained which did not exhibit hemolytic properties and which formed viscous colonies when spread on a blood agar medium (available from Eiken Kagaku Co., Japan). This mutant, *Streptococcus zooepidemicus* NH-131 has been deposited in the Fermentation Research Institute (Japan).

The *Streptococcus zooepidemicus* NH-131 (i.e., FERM BP-784) was subjected to shake culture in a test tube containing a brain heart infusion culture medium. When equinus blood was added to the resultant cultivated mixture and was allowed to stand at a temperature of 37° C. for 2 hours, the erythroyte precipitated at the bottom of the test tube and the supernate exhibited the color of the culture medium itself. Thus, it was confirmed that this mutant had no hemolytic properties.

Example 2

A culture medium composed of 6% of glucose, 0.5% yeast extract (available from Oriental Yeast Co., Japan), 1.0% of polypeptone (available from Daigo Eiyo Kagaku Co. Japan), and 0.005% of Adekanol LG-805 (i.e., polyether type antifoamant available from Asahi Denka Kogyo Co. Japan) was used. 10 liters of the culture medium except for the glucose was charged into a 30 liter jar fermenter. After sterilization at a temperature of 121° C. for 20 minutes, the *Streptococcus zooepidemicus* NH-131 previously cultivated was inoculated into the culture medium. The aeration spinner culture was carried out at a temperature of 35° C. for 2 days while controlling the pH of the medium to 7.0 with sodium hydroxide.

The glucose was sterilized separately to the culture medium and a 0.2% portion of the 6% glucose was added to the jar fermenter at the start of the cultivation and the remaining 5.8% start was added around the beginning of the logarithmic growth (i.e., 5 to 7 hours after the start of the cultivation). The cultivation progress conditions were as shown in FIG. 1 in which the changes in the production amount (g/l) of the hyaluronic acid (x-x), the glucose amount (%) ( - ), and the cell growth $OD_{660}$ (o-o) with the elapse of the cultivation time are graphically illustrated.

The determination of these changes was carried out as follows:

(1) The production amount of hyaluronic acid was determined by weighing the purified hyaluronic acid isolated from a sample.
(2) The glucose amount was determined by a YSI model 27 sugar analyzer (manufactured by Yellow Springs Instrument Co., U.S.A.).
(3) The cell growth was determined by measuring the absorbance of a sample at 660 nm in a spectrophotometer.

The production amount of the desired pyaluronic acid was increased with the elapse of time, and the viscosity of the cultivation mixture was increased. Thus, the cultivation was stopped when the viscosity of the cultivation mixture became almost maximum (after one or two days from the start of the cultivation).

The cultivation mixture was centrifugally treated to separate and remove the insoluble components from the mixture. The protein components present in the resultant mixture were removed by a mixture of chloroform and isoamyl alcohol (5:1) and the low molecular weight substances contained in the resultant mixture were then removed by ultrafiltration. Finally, 3.6 g of the desired hyaluronic acid was recovered from 1 liter of the cultivated liquid by a freeze-drying method.

Figure 2:
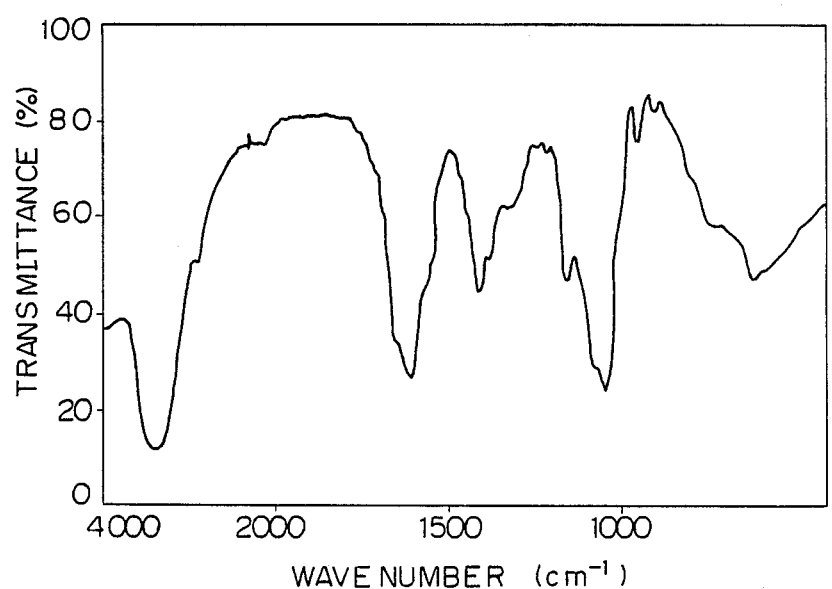
FIG. 2 is an infrared absorption spectrum of hyaluronic acid obtained in Example 2.

The hyaluronic acid product thus obtained in the form of white fiber was soluble in water but insoluble in organic solvents such as methanol, ethanol, acetone, chloroform, and ether, and had no taste and no odor. The product was confirmed as hyaluronic acid by an infrared absorption spectrum, and electrophoresis, and a decomposition test by fungus hyaluronidase. The infrared absorption spectrum of the resultant hyaluronic acid was as shown in FIG. 2.

We claim:

1. A method of preparing hyaluronic acid free from streptolysin comprising the steps of:
   a. obtaining an anhemolytic mutant of Streptococcus zooepidemicus microorganisms capable of producing hyaluronic acid;
   b. growing a culture of said anhemolytic mutant;
   c. recovering hyaluronic acid free from streptolysin from said culture of anhemolytic mutant.

2. The method of claim 1 wherein said anhemolytic mutant is obtained by the selective isolation of cultured Streptococcus zooepidemicus microorganisms having decreased hemolysis.

3. The method of claim 2 wherein said microorganisms having decreased hemolysis are subjected to UV or N-methyl-N'-nitro-N-nitrosoguanidine mutation treatment.

4. The method of claim 3, wherein said microorganisms subjected to mutation treatment which exhibit viscous colony growth and are anhemolytic are recovered.

5. The method of claim 1, wherein said anhemolytic mutant is *Streptococcus zooepidemicus* FERM BP-784.

* * * * *